US00PP13704P29

(12) United States Plant Patent
Hofmann

(10) Patent No.: US PP13,704 P2
(45) Date of Patent: Apr. 1, 2003

(54) NEW GUINEA IMPATIENS PLANT NAMED 'FISIMP 413'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/087,965

(22) Filed: Mar. 4, 2002

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisimp 413', characterized by its upright and outwardly spreading, tall and uniformly mounded plant habit; freely branching and freely flowering habit; large rounded white-colored flowers with red purple-colored markings and eye that are positioned above and beyond the foliage; and very dark green-colored leaves.

1 Drawing Sheet

BOTANICAL CLASSIFICATION/CULTIVAR DESIGNATION

*Impatiens hawkeri* cultivar Fisimp 413.

BACKGROUND OF THE INVENTION

The present Invention relates to a new and distinct cultivar of New Guinea Impatiens plant, botanically known as *Impatiens hawkeri*, and hereinafter referred to by the name 'Fisimp 413'.

The new Impatiens is a product of a planned breeding program conducted by the Inventor in Hillscheid, Germany. The objective of the breeding program is to develop new vigorous Impatiens cultivars that flower relatively early with large rounded flowers and attractive flower colors.

The new Impatiens originated from a cross made by the Inventor in July, 1997 of the *Impatiens hawkeri* cultivar Danharwt, not patented, as the female, or seed, parent with the *Impatiens hawkeri* cultivar Dueripinkeye, disclosed in U.S. Plant Pat. No. 11,320, as the male, or pollen, parent. The cultivar Fisimp 413 was discovered and selected by the Inventor as a flowering plant within the progeny of the stated cross in a controlled environment in Moncarapacho, Portugal in March, 1998.

Asexual reproduction of the new cultivar by terminal cuttings taken in Moncarapacho, Portugal, since March, 1998, has shown that the unique features of this new Impatiens are stable and reproduced true to type in successive generations.

SUMMARY OF THE INVENTION

The following traits have been repeatedly observed and are determined to be the unique characteristics of 'Fisimp 413'. These characteristics in combination distinguish 'Fisimp 413' as a new and distinct Impatiens cultivar:

1. Upright and outwardly spreading, tall and uniformly mounded plant habit.

2. Freely branching and freely flowering habit.

3. Large rounded white-colored flowers with red purple-colored markings and eye that are positioned above and beyond the foliage.

4. Very dark green-colored leaves.

Plants of the new Impatiens can be compared to plants of the female parent, the cultivar Danharwt. In side-by-side comparisons conducted by the Inventor in Hillscheid, Germany, plants of the new Impatiens differed from plants of the cultivar Danharwt in the following characteristics:

1. Plants of the new Impatiens were more vigorous and larger than plants of the cultivar Danharwt.

2. Plants of the new Impatiens had darker green-colored leaves than plants of the cultivar Danharwt.

3. Flowers of plants of the new Impatiens were white-colored with red purple-colored markings and eye whereas flowers of plants of the cultivar Danharwt were solid white in color.

Plants of the new Impatiens can be compared to plants of the male parent, the cultivar Dueripinkeye. In side-by-side comparisons conducted by the Inventor in Hillscheid, Germany, plants of the new Impatiens differed from plants of the cultivar Dueripinkeye in the following characteristics:

1. Plants of the new Impatiens were more vigorous and larger than plants of the cultivar Dueripinkeye.

2. Plants of the new Impatiens flowered later than plants of the cultivar Dueripinkeye.

3. Flowers of plants of the new Impatiens were white-colored with red purple-colored markings and eye whereas flowers of plants of the cultivar Dueripinkeye were light pink-colored with a pink-colored eye.

Plants of the new Impatiens can also be compared to plants of the cultivar BSR-202 Blush White, disclosed in U.S. Plant Pat. No. 8,848. In side-by-side comparisons conducted by the Inventor in Hillscheid, Germany, plants of the new Impatiens differed from plants of the cultivar BSR-202 Blush White in the following characteristics:

1. Plants of the new Impatiens were taller and more vigorous than plants of the cultivar BSR-202 Blush White.

2. Plants of the new Impatiens had longer internodes than plants of the cultivar BSR-202 Blush White.

3. Flowers of plants of the new Impatiens were larger and flatter than flowers of plants of the cultivar BSR-202 Blush White.

4. Flowers of plants of the new Impatiens were white-colored with red purple-colored markings and eye whereas flowers of plants of the cultivar BSR-202 Blush White were light pink-colored with a small purple-colored eye.

Plants of the new Impatiens can also be compared to plants of the cultivar Improved Samoa, disclosed in U.S. Plant Pat. No. 9,138. In side-by-side comparisons conducted by the Inventor in Hillscheid, Germany, plants of the new Impatiens differed from plants of the cultivar Improved Samoa in the following characteristics:

1. Plants of the new Impatiens were taller and more vigorous than plants of the cultivar Improved Samoa.

2. Plants of the new Impatiens had larger flowers than plants of the cultivar Improved Samoa.

3. Flowers of plants of the new Impatiens were white-colored with red purple-colored markings and eye whereas flowers of plants of the cultivar Improved Samoa were white-colored with a purple-colored eye.

Plants of the new Impatiens can also be compared to plants of the cultivar Danharras, not patented. In side-by-side comparisons conducted by the Inventor in Hillscheid, Germany, plants of the new Impatiens differed from plants of the cultivar Danharras in the following characteristics:

1. Plants of the new Impatiens were taller and more vigorous than plants of the cultivar Danharras.

2. Flowers of plants of the new Impatiens were white-colored with red purple-colored markings and eye whereas flowers of plants of the cultivar Danharras were white to pale pink-colored with faint pink-colored markings and a purple-colored eye.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisimp 413' grown in a container.

DETAILED BOTANICAL DESCRIPTION

The cultivar Fisimp 413 has not been observed under all possible environmental conditions. The phenotype may vary somewhat with variations in environment such as temperature and light intensity, without, however, any variance in genotype.

The aforementioned photograph, following observations and measurements describe plants grown in Langley, British Columbia, Canada, under commercial practice in a greenhouse. Rooted young plants were planted in 17.5-cm containers during the spring and the aforementioned photograph and following observations and measurements were taken during the summer about 17 weeks later. During the production of the plants, day temperatures ranged from 21 to 24° C. and night temperatures were about 17 to 18° C. In the following description, color references are made to The Royal Horticultural Society Colour Chart, 1995 Edition, except where general terms of ordinary dictionary significance are used.

Botanical classification: *Impatiens hawkeri* cultivar Fisimp 413.

Parentage:

*Female parent.*—*Impatiens hawkeri* cultivar Danharwt, not patented.

*Male parent.*—*Impatiens hawkeri* cultivar Dueripinkeye, disclosed in U.S. Plant Pat. No. 11,320.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 159A in color.

Plant description:

*General appearance.*—Upright and outwardly spreading, tall and uniformly mounded plant growth habit; freely branching habit, dense and bushy appearance; freely flowering. Vigorous.

*Crop time.*—From a rooted cutting, about 10 to 11 weeks are required to produce finished flowering plants in 12-cm containers.

*Plant height.*—About 29.2 cm.

*Plant diameter or spread.*—About 58.1 cm.

*Lateral branches.*—Quantity per plant: About 14. Length: About 24.5 cm. Diameter: About 1.1 cm. Internode length: About 8.75 cm. Texture: Smooth, glabrous. Color: Young stems, 144A; older stems, 181B.

*Foliage description.*—Arrangement: Primarily in whorls. Length: About 12.4 cm. Width: About 4.85 cm. Shape: Elliptic. Apex: Acute to acuminate. Base: Acute. Margin: Serrulate with ciliation. Texture: Smooth, slightly rugose; glabrous. Color: Young foliage, upper surface: 139A. Young foliage, lower surface: 185A. Fully expanded foliage, upper surface: Much darker than 139A. Fully expanded foliage, lower surface: 187C. Venation, upper surface: 53C. Venation, lower surface: 60A. Petiole: Length: About 3.25 cm. Diameter: About 3.5 mm. Texture: Smooth, glabrous. Color: Upper surface: 47A. Lower surface: 60A.

Flower description:

*Flower type and flowering habit.*—Single; large rounded white-colored flowers with red purple-colored markings and eye; mostly flat. Freely and continuously flowering; usually about 7 to 10 flowers and flower buds per lateral branch. Flowers positioned above and beyond the foliage and typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 10 weeks after planting.

*Flower buds.*—Length: About 2.5 cm. Diameter: About 1.9 cm. Shape: Ovoid. Color: 66B to 66C, becoming 155D with development.

*Flower length.*—About 8.1 cm.

*Flower width.*—About 7.9 cm.

*Flower depth.*—About 1.25 cm.

*Petals.*—Quantity: Five per flower, imbricate. Length: Banner petals: About 3.1 cm. Lateral and base petals: About 3.6 cm. Width: Banner petal: About 6 cm.

Lateral and base petals: About 4.5 cm. Shape: Roughly cordate. Apex: Emarginate. Base: Attenuate. Margin: Entire. Aspect: Mostly flat. Texture: Smooth; satiny. Color: When opening, upper surface: Ground color, 155D; longitudinal central stripe on banner petal; 68A to 68B. When opening, lower surface: Ground color, 155D; longitudinal central stripe on banner petal and very fine and faint longitudinal lines on lateral and base petals; 66B to 66C. Fully opened, upper surface: Ground color, 155D; longitudinal central stripe on banner petal and very fine and faint longitudinal lines on lateral and base petals; 68B; towards base of petals or eye, 74B. Fully opened, lower surface: Ground color, 155D; longitudinal central stripe on banner petal; 66B to 66C.

*Spur.*—Quantity: One per flower. Length: About 6.5 cm. Diameter: At apex: About 0.5 mm. At flower: About 2.5 mm. Aspect: Curved. Color: Towards flower, 49B; towards apex, 145B.

*Peduncles.*—Length: About 6.3 cm. Diameter: About 2 mm. Texture: Smooth, glabrous. Strength: Strong, flexible. Angle: About 45° from the lateral branch. Color: 144C overlain with 180D.

*Reproductive organs.*—Androecium: Stamen number: Five fused at anthers, hooded; filaments free. Anther length: About 5 mm. Anther shape: Obovate. Anther color: 74C. Pollen amount: Moderate. Pollen color: 8D. Gynoecium: Pistil quantity: One per flower. Pistil length: About 4.5 mm. Stigma color: 54A. Style color: 54A. Ovary: Five-celled. Ovary color: Initially 147B, becoming 183A with development.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisimp 413', as illustrated and described.

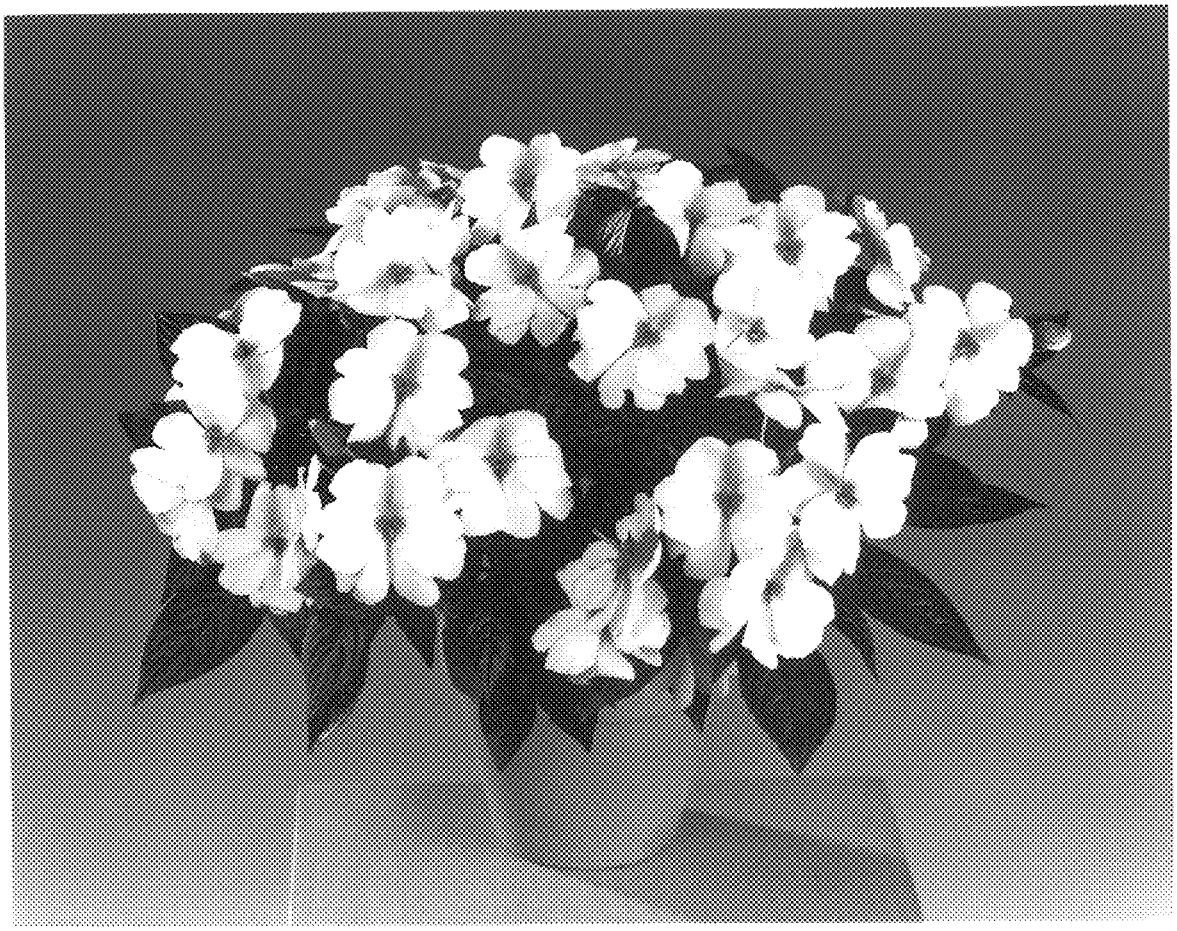

* * * * *